United States Patent
Cottard et al.

(10) Patent No.: US 7,766,977 B2
(45) Date of Patent: *Aug. 3, 2010

(54) DYE COMPOSITION OF ACIDIC PH COMPRISING 2,3-DIAMINO-6,7-DIHYDRO-1H,5H-PYRAZOLO[1,2-A]PYRAZOL-1-ONE, A PARA-PHENYLENEDIAMINE, A META-AMINOPHENOL AND AN OXIDIZING AGENT, AND PROCESSES FOR DYEING KERATIN FIBERS USING THE COMPOSITION

(75) Inventors: François Cottard, Courbevoie (FR); Florence Laurent, Bois Colombes (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/987,451

(22) Filed: Nov. 30, 2007

(65) Prior Publication Data

US 2009/0007347 A1 Jan. 8, 2009

Related U.S. Application Data

(60) Provisional application No. 60/874,272, filed on Dec. 12, 2006.

(30) Foreign Application Priority Data

Nov. 30, 2006 (FR) .................................. 06 55214

(51) Int. Cl.
*A61Q 5/10* (2006.01)
(52) U.S. Cl. .................. 8/405; 8/406; 8/407; 8/408; 8/410; 8/411; 8/412; 8/421; 8/567
(58) Field of Classification Search ............. 8/405, 8/406, 407, 408, 410, 411, 412, 421, 567; 548/369.1
See application file for complete search history.

(56) References Cited

U.S. PATENT DOCUMENTS

| | | | |
|---|---|---|---|
| 3,012,884 A | 12/1961 | de Ramaix et al. |
| 4,003,699 A | 1/1977 | Rose et al. |
| 4,128,425 A | 12/1978 | Greenwald |
| RE30,199 E | 1/1980 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,718,731 A | 2/1998 | Loewe et al. |
| 5,766,576 A | 6/1998 | Löwe et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,436,151 B2 | 8/2002 | Cottard et al. |
| 6,645,258 B2 | 11/2003 | Vidal et al. |
| 6,660,046 B1 | 12/2003 | Terranova et al. |
| 6,730,789 B1 | 5/2004 | Birault et al. |
| 7,285,137 B2 | 10/2007 | Vidal et al. |
| 7,485,156 B2 | 2/2009 | Saunier |
| 7,488,355 B2 | 2/2009 | Saunier |
| 7,488,356 B2 | 2/2009 | Saunier |
| 2001/0023514 A1 | 9/2001 | Cottard et al. |
| 2002/0046431 A1 | 4/2002 | Laurent et al. |
| 2002/0050013 A1 | 5/2002 | Vidal et al. |
| 2002/0088062 A1 | 7/2002 | Pratt |
| 2003/0019051 A9 | 1/2003 | Vidal et al. |
| 2005/0166335 A1* | 8/2005 | Vidal et al. .................. 8/405 |
| 2007/0006398 A1 | 1/2007 | Hercouet |
| 2008/0005853 A1 | 1/2008 | Cottard et al. |
| 2008/0016627 A1 | 1/2008 | Cottard et al. |
| 2008/0016628 A1 | 1/2008 | Cottard et al. |
| 2009/0007347 A1 | 1/2009 | Cottard et al. |

FOREIGN PATENT DOCUMENTS

| | | |
|---|---|---|
| CH | 421 343 | 9/1966 |
| DE | 1 959 009 | 12/1970 |
| DE | 23 59 399 | 6/1975 |
| DE | 38 43 892 | 6/1990 |

(Continued)

OTHER PUBLICATIONS

English language abstract of DE 101 48 847 A1, May 10, 2003.

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a composition for dyeing keratin fibers, for example, human keratin fibers such as the hair, comprising at least one first oxidation base chosen from 2,3-diamino-6,7-dihydro-1H,5H-pyrazolo[1,2-a]pyrazol-1-one and the addition salts thereof, at least one second oxidation base chosen from para-phenylenediamines, at least one coupler chosen from meta-aminophenols and at least one oxidizing agent, the pH of the composition ranging from 5.5 to 7.5. The present disclosure makes it possible to obtain a coloration on keratin fibers with tints in red, coppery or mahogany tones that are sufficiently visible on natural or dyed hair and uniform from the roots to the ends.

12 Claims, No Drawings

FOREIGN PATENT DOCUMENTS

| | | |
|---|---|---|
| DE | 41 33 957 | 4/1993 |
| DE | 195 43 988 | 5/1997 |
| DE | 196 19 112 | 11/1997 |
| DE | 101 48 847 A1 | 5/2003 |
| EP | 0 770 375 | 5/1997 |
| EP | 0 873 745 | 10/1998 |
| EP | 1 250 909 | 10/2002 |
| EP | 1 550 656 A1 | 7/2005 |
| FR | 2 586 913 | 3/1987 |
| FR | 2 733 749 | 11/1996 |
| FR | 2 750 048 | 12/1997 |
| FR | 2 801 308 | 5/2001 |
| FR | 2 886 132 | 12/2006 |
| FR | 2 886 135 | 12/2006 |
| FR | 2 886 136 | 12/2006 |
| FR | 2 886 137 | 12/2006 |
| FR | 2 886 138 | 12/2006 |
| FR | 2 886 139 | 12/2006 |
| FR | 2 886 140 | 12/2006 |
| FR | 2 886 141 | 12/2006 |
| FR | 2 886 142 | 12/2006 |
| FR | 2 902 323 | 12/2007 |
| FR | 2 902 327 | 12/2007 |
| FR | 2 902 328 | 12/2007 |
| GB | 1 005 233 | 9/1965 |
| GB | 1 026 978 | 4/1966 |
| GB | 1 153 196 | 5/1969 |
| GB | 1 486 76 | 11/1974 |
| JP | 2-19576 | 1/1990 |
| JP | 05 163 124 | 6/1993 |
| JP | 2002-535312 | 10/2002 |
| WO | WO 94/08969 | 4/1994 |
| WO | WO 94/08970 | 4/1994 |
| WO | WO 96/15765 | 5/1996 |

OTHER PUBLICATIONS

English language abstract of EP 0 770 375 B1, May 2, 1997.
English language esp@cenet abstract of FR 2 801 308, May 25, 2001.
English language abstract of JP 2-19576, Jan. 23, 1990.
English language abstract of JP 5-163124, Jun. 29, 1993.
EP Search Report for EP 07121666.7, dated Apr. 2, 2008 and corresponding to present application.
French Search Report for FR 0652557, dated Mar. 9, 2007.
French Search Report for FR 0652558, dated Mar. 9, 2007.
French Search Report for FR 0652549, dated Mar. 6, 2007.
French Search Report for FR 0655213, dated Jul. 24, 2007 (corresponding to present application).
Office Action dated Oct. 27, 2008, in co-pending U.S. Appl. No. 11/987,450.
Office Action dated Aug. 4, 2008, in co-pending U.S. Appl. No. 11/812,603.
Office Action dated Aug. 6, 2008, in co-pending U.S. Appl. No. 11/812,610.
Co-pending U.S. Appl. No. 10/999,999, filed Dec. 1, 2004.
Co-pending U.S. Appl. No. 11/812,603, filed Jun. 20, 2007.
Co-pending U.S. Appl. No. 11/812,610, filed Jun. 20, 2007.
Co-pending U.S. Appl. No. 11/812,616, filed Jun. 20, 2007.
Co-pending U.S. Appl. No. 11/898,438, filed Sep. 12, 2007.
Co-pending U.S. Appl. No. 11/987,450, filed Nov. 30, 2007.
English language Abstract of DE 1 959 009, dated Dec. 3, 1970.
English language Abstract of DE 196 19 112, dated Nov. 13, 1997.
English language Abstract of EP 0 873 745, dated Oct. 28, 1998.
English language Abstract of EP 1 250 909, dated Oct. 23, 2002.
English language Abstract of FR 2 886 135, dated Dec. 1, 2006.
English language Abstract of FR 2 886 136, dated Dec. 1, 2006.
English language Abstract of FR 2 886 140, dated Dec. 1, 2006.
English language Abstract of FR 2 886 141, dated Dec. 1, 2006.
English language Abstract of FR 2 886 142, dated Dec. 1, 2006.
French Search Report for FR 06/55214, dated Jul. 25, 2007.
Helvetica Chimica Acta., vol. XXXIII, Fasciculus V (1950), No. 152, pp. 1183-1194.
Morissette et al., Advanced Drug Delivery Reviews, 2004, 56, pp. 275-300.
Notice of Allowance mailed Jun. 26, 2007, in co-pending U.S. Appl. No. 10/999,999.
Notice of Allowance mailed Mar. 9, 2007, in co-pending U.S. Appl. No. 10/999,999.
Notice of rejection in counterpart Japanese Application No. 2004-348020, mailed Dec. 6, 2005.
Notice of rejection in counterpart Japanese Application No. 2004-348020, mailed Jan. 29, 2008.
Office Action mailed Apr. 14, 2009, in co-pending U.S. Appl. No. 11/812,616.
Office Action mailed Apr. 16, 2009, in co-pending U.S. Appl. No. 11/812,610.
Office Action mailed Aug. 15, 2008, in co-pending U.S. Appl. No. 11/812,616.
Office Action mailed Mar. 2, 2009, in co-pending U.S. Appl. No. 11/898,438.
Office Action mailed Mar. 24, 2009, in co-pending U.S. Appl. No. 11/812,603.
Office Action mailed May 1, 2009, in co-pending U.S. Appl. No. 11/987,450.
Office Action mailed Sep. 22, 2009, in co-pending U.S. Appl. No. 11/812,616.
STIC Search Report for U.S. Appl. No. 10/999,999, dated Dec. 13, 2006.
STIC Search Report for U.S. Appl. No. 11/812,603, dated Jul. 13, 2008.
STIC Search Report for U.S. Appl. No. 11/812,610, dated Jul. 31, 2008.
Vippagunta, S.R., "Crystalline Solids," Advanced Drug Delivery Reviews, 2001, 48, pp. 3-26.

* cited by examiner

DYE COMPOSITION OF ACIDIC PH COMPRISING 2,3-DIAMINO-6,7-DIHYDRO-1H,5H-PYRAZOLO[1,2-A]PYRAZOL-1-ONE, A PARA-PHENYLENEDIAMINE, A META-AMINOPHENOL AND AN OXIDIZING AGENT, AND PROCESSES FOR DYEING KERATIN FIBERS USING THE COMPOSITION

This application claims benefit of U.S. Provisional Application No. 60/874,272, filed Dec. 12, 2006, the contents of which are incorporated herein by reference. This application also claims benefit of priority under 35 U.S.C. §119 to French Patent Application No. FR 0655214, filed Nov. 30, 2006, the contents of which are also incorporated herein by reference.

The present disclosure relates to a composition for dyeing keratin fibers, for example human keratin fibers such as the hair, comprising 2,3-diamino-6,7-dihydro-1H,5H-pyrazolo[1,2-a]pyrazol-1-one or an addition salt thereof as a first oxidation base, at least one para-phenylenediamine as a second oxidation base, at least one meta-aminophenol as a coupler and at least one oxidizing agent, wherein the pH of the composition ranges from 5.5 to 7.5.

It is known practice to dye keratin fibers, for example human keratin fibers such as the hair, with dye compositions comprising oxidation dye precursors, such as ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives, which are generally known as oxidation bases. Oxidation dye precursors, or oxidation bases, are colorless or weakly colored compounds that, when combined with oxidizing products, can give rise to dyes or colored compounds via a process of oxidative condensation. Permanent colorations are thus obtained.

It is also known that the shades obtained with these oxidation bases may be varied by combining them with couplers or coloration modifiers, for example, meta-phenylenediamines, meta-aminophenols, meta-hydroxyphenols, and certain heterocyclic compounds.

The variety of molecules that may be used as oxidation bases and couplers allows a wide range of colors to be obtained.

However, the use of standard oxidation bases such as para-aminophenol, ortho-aminophenol and derivatives thereof optionally combined with standard couplers at acidic pH often does not make it possible to obtain shades with tints in red, coppery or mahogany tones that are sufficiently visible on natural or dyed hair, and/or which are uniform from the roots of the hair to the ends.

The present disclosure provides novel compositions for dyeing keratin fibers that make it possible to obtain, at acidic pH, a coloration with tints in red, coppery or mahogany tones that are particularly visible, strong, chromatic, aesthetic, and/or sparingly selective. In addition, these colorations may be resistant to one or more of the various attacking factors to which the fibers may be subjected, such as shampoo, light, sweat, and permanent reshaping operations.

Thus, the present disclosure relates to, in one aspect, a composition for dyeing keratin fibers, comprising, in a suitable dyeing medium:

at least one first oxidation base chosen from 2,3-diamino-6,7-dihydro-1H,5H-pyrazolo[1,2-a]pyrazol-1-one of formula (I) below, and the addition salts thereof:

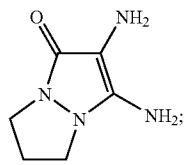

(I)

at least one second oxidation base chosen from para-phenylenediamines;

at least one first coupler chosen from meta-aminophenols; and at least one oxidizing agent;

wherein the pH of the composition ranges from 5.5 to 7.5.

The composition of the present disclosure makes it possible to obtain a coloration on keratin fibers with tints in red, coppery or mahogany tones that are sufficiently visible on natural or dyed hair and/or which is uniform from the roots to the ends.

The present disclosure also relates to a process for dyeing keratin fibers, for example human keratin fibers such as the hair, using the compositions described herein, and also the use of these compositions for dyeing keratin fibers.

The present disclosure further relates to a dyeing kit comprising, firstly, a dye composition containing 2,3-diamino-6,7-dihydro-1H,5H-pyrazolo[1,2-a]pyrazol-1-one or an addition salt thereof as first oxidation base, a para-phenylenediamine as second oxidation base and a meta-aminophenol as coupler and, secondly, a composition containing an oxidizing agent.

Unless otherwise indicated, the limits of the ranges of values provided herein are included in these ranges.

As used herein, the term "alkyl radical" means, unless otherwise indicated, linear or branched $C_1$-$C_{10}$ (for example, $C_1$-$C_6$ or $C_1$-$C_4$) alkyl radicals. Non-limiting examples of such alkyl radicals include methyl, ethyl, propyl, isopropyl, isobutyl, tert-butyl, pentyl, and hexyl radicals.

As used herein, the term "heteroatom," unless otherwise indicated, means an atom chosen from oxygen, nitrogen, sulfur, and phosphorus atoms.

As used herein, the term, "halogen atom," unless otherwise indicated, means an atom chosen from chlorine, bromine, iodine, and fluorine atoms.

The at least one oxidation base chosen from 2,3-diamino-6,7-dihydro-1H,5H-pyrazolo[1,2-a]pyrazol-1-one of formula (I) and the addition salts thereof is, in at least one embodiment, present in the composition of the present disclosure in an amount, for each if there are more than one, ranging from 0.001% to 10%, for example, from 0.005% to 6% by weight, relative to the total weight of the composition.

According to a non-limiting embodiment of the present disclosure, the at least one second oxidation base is a para-phenylenediamine chosen from the compounds of formula (II) below, and the addition salts thereof:

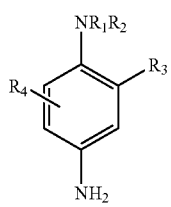

(II)

wherein:

$R_1$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical, and a $C_1$-$C_4$ alkyl radical substituted with a nitrogenous, phenyl or 4'-aminophenyl group;

$R_2$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical, and a $C_1$-$C_4$ alkyl radical substituted with a nitrogenous group; or $R_1$ and $R_2$ may form, together with the nitrogen atom to which they are attached, a 5- or 6-membered, saturated or unsaturated cyclic group containing at least one heteroatom, optionally substituted with at least one group chosen from alkyl, hydroxyl and ureido groups;

$R_3$ is chosen from a hydrogen atom, a halogen atom (such as chlorine), a $C_1$-$C_4$ alkyl radical, a sulfo radical, a carboxy radical, a $C_1$-$C_4$ monohydroxyalkyl radical or $C_1$-$C_4$ hydroxyalkoxy radical, an acetylamino$(C_1$-$C_4)$alkoxy radical, a mesylamino$(C_1$-$C_4)$alkoxy radical, and a carbamoylamino$(C_1$-$C_4)$alkoxy radical, $R_4$ is chosen from a hydrogen atom, a halogen atom, and a $C_1$-$C_4$ alkyl radical.

As examples of suitable nitrogenous groups, non-limiting mention may be made of amino, mono$(C_1$-$C_4)$alkylamino, di$(C_1$-$C_4)$alkylamino, tri$(C_1$-$C_4)$alkylamino, monohydroxy $(C_1$-$C_4)$alkylamino, imidazolinium, and ammonium radicals.

As examples of the para-phenylenediamines of formula (II) above, non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(□-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-β-hydroxyethylamino-5-aminotoluene, 2-methyl-7-N-β-hydroxyethyl-para-phenylenediamine and 3-hydroxy-1-(4'-aminophenyl)pyrrolidine, and the acid-addition salts thereof.

Among the para-phenylenediamines of formula (II) above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine 2-β-acetylaminoethyloxy-para-phenylenediamine and 6-(4-aminophenylamino)hexan-1-ol, and the acid addition salts thereof.

In the composition of the present disclosure, the at least one second oxidation base chosen from para-phenylenediamines is, in at least one embodiment, present in an amount, for each if there are more than one, ranging from 0.001% to 10%, for example from 0.005% to 6% by weight, relative to the total weight of the dye composition.

In at least one embodiment of the present disclosure, the at least one first coupler is chosen from meta-aminophenols of the compounds of formula (III) below, and the addition salts thereof:

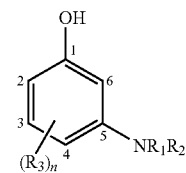

(III)

wherein:

$R_1$ and $R_2$, which may be identical or different, are chosen from a hydrogen atom; alkyl radicals; monohydroxyalkyl radicals; polyhydroxyalkyl radicals; and monoaminoalkyl radicals; or $R_1$ and $R_2$ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino and dialkylamino radicals and alkyl radicals optionally substituted with at least one radical chosen from hydroxyl, amino, monoalkylamino, and dialkylamino radicals;

n is an integer ranging from 0 to 3; and $R_3$, which may be identical or different if n is greater than 1, is chosen from a halogen atom, an alkyl radical, an alkoxy radical, a monohydroxyalkyl radical, a polyhydroxyalkyl radical, a monohydroxyalkoxy radical, and a polyhydroxyalkoxy radical.

In at least one embodiment of the present disclosure, $R_1$ and $R_2$ of formula (III) are each independently chosen from a hydrogen atom; alkyl radicals, for example methyl and ethyl radicals; monohydroxyalkyl radicals, for example β-hydroxyethyl and γ-hydroxypropyl radicals; or $R_1$ and $R_2$ may form, together with the nitrogen atom to which they are attached, a ring chosen from pyrrolidine, piperidine, homopiperidine, piperazine, homopiperazine and morpholine heterocycles; said rings being optionally substituted with at least one radical chosen from hydroxyl, amino, mono$(C_1$-$C_2)$alkylamino, di$(C_1$-$C_2)$alkylamino, carboxyl and carboxamido radicals, or from $C_1$-$C_4$ alkyl radicals optionally substituted with at least one radical chosen from hydroxyl, amino, mono $(C_1$-$C_2)$alkylamino, and di$(C_1$-$C_2)$alkylamino radicals.

As examples of such rings, non-limiting mention may be made of pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(β-hydroxyethyl)-aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-(2-hydroxyethyl)homopiperazine, piperazine, 4-methylpiperazine, 4-ethylpiperazine, 4-(β-hydroxyethyl)piperazine and morpholine, which may, in at least one embodiment, form the following groups: pyrrolidin-1-yl; piperidin-1-yl; piperazin-1-yl; 4-methylpiperazin-1-yl; 4-ethylpiperazin-1-yl; and 4-(β-hydroxyethyl)piperazin-1-yl; morpholin-4-yl.

In at least one embodiment of the present disclosure, $R_3$ of formula (III) is independently chosen from a halogen atom, an alkyl radical, an alkoxy radical and a monohydroxyalkoxy radical. For example, each $R_3$ may be independently chosen from a chlorine atom, a methyl radical, a methoxy radical and a β-hydroxyethyloxy radical.

In at least one embodiment of the present disclosure, n is an integer ranging from 0 to 2. For example, n may be 1 or 2. In at least one embodiment, when n is equal to 1, $R_3$ may be in position 2 of formula (III), and when n is equal to 2, $R_3$ may be in positions 2 and 4 or in positions 2 and 6 of formula (III).

Among the substituted meta-aminophenols of formula (III), non-limiting mention may be made of 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 6-chloro-2-methyl-5-aminophenol, 5-amino-2,4-dimethoxyphenol, 5-(γ-hydroxypropylamino)-2-methylphenol, 3-dimethylaminophenol; 2-methyl-5-dimethylaminophenol; 2-ethyl-5-dimethylaminophenol; 2-methoxy-5-dimethylaminophenol; 2-ethoxy-5-dimethylaminophenol; 2-(β-hydroxyethyl)-5-dimethylaminophenol; 3-diethylaminophenol; 2-methyl-5-diethylaminophenol; 2-ethyl-5-diethylaminophenol; 2-methoxy-5-diethylaminophenol; 2-ethoxy-5-diethylaminophenol; 2-(β-hydroxyethyl)-5-diethylaminophenol; 3-di(β-hydroxyethyl)aminophenol; 2-methyl-5-di(β-hydroxyethyl)aminophenol; 2-ethyl-5-di(β-hydroxyethyl)aminophenol; 2-methoxy-5-di(β-hydroxyethyl)aminophenol; 2-ethoxy-5-di(β-hydroxyethyl)aminophenol; 2-(β-hydroxyethyl)-5-di(β-hydroxyethyl)aminophenol; 3-pyrrolidin-1-ylphenol; 2-methyl-5-pyrrolidin-1-ylphenol, 2-ethyl-5-pyrrolidin-1-ylphenol; 2-methoxy-5-pyrrolidin-1-ylphenol; 2-ethoxy-5-pyrrolidin-1-ylphenol; 2-(β-hydroxyethyl)-5-pyrrolidin-1-ylphenol; 3-piperidin-1-ylphenol; 2-methyl-5-piperidin-1-ylphenol; 2-ethyl-5-piperidin-1-ylphenol; 2-methoxy-5-piperidin-1-ylphenol; 2-ethoxy-5-piperidin-1-ylphenol; 2-(β-hydroxyethyl)-5-piperidin-1-ylphenol; 3-piperazin-1-ylphenol; 2-methyl-5-piperazin-1-ylphenol; 2-ethyl-5-piperazin-1-ylphenol; 2-methoxy-5-piperazin-1-ylphenol; 2-ethoxy-5-piperazin-1-ylphenol; 2-(β-hydroxyethyl)-5-piperazin-1-ylphenol; 3-(4-methylpiperazin-1-yl)phenol; 2-methyl-5-(4-methylpiperazin-1-yl)phenol; 2-ethyl-5-(4-methylpiperazin-1-yl)phenol; 2-methoxy-5-(4-methylpiperazin-1-yl)phenol; 2-ethoxy-5-(4-methylpiperazin-1-yl)phenol; 2-(β-hydroxyethyl)-5-(4-methylpiperazin-1-yl)phenol; 3-(4-ethylpiperazin-1-yl)phenol; 2-methyl-5-(4-ethylpiperazin-1-yl)phenol; 2-ethyl-5-(4-ethylpiperazin-1-yl)phenol; 2-methoxy-5-(4-ethylpiperazin-1-yl)phenol; 2-ethoxy-5-(4-ethylpiperazin-1-yl)phenol; 2-(β-hydroxyethyl)-5-(4-ethylpiperazin-1-yl)phenol; 3-(4-(β-hydroxyethyl)piperazin-1-yl)phenol; 2-methyl-5-(4-(β-hydroxyethyl)piperazin-1-yl)phenol; 2-ethyl-5-(4-(β-hydroxyethyl)piperazin-1-yl)phenol; 2-methoxy-5-(4-(β-hydroxyethyl)piperazin-1-yl)phenol; 2-ethoxy-5-(4-(β-hydroxyethyl)piperazin-1-yl)phenol; 2-(β-hydroxyethyl)-5-(4-(β-hydroxyethyl)piperazin-1-yl)phenol; 3-morpholin-4-ylphenol; 2-methyl-5-morpholin-4-ylphenol; 2-ethyl-5-morpholin-4-ylphenol; 2-methoxy-5-morpholin-4-ylphenol; 2-ethoxy-5-morpholin-4-ylphenol; and 2-(β-hydroxyethyl)-5-morpholin-4-ylphenol.

In at least one embodiment of the present disclosure, $R_1$ and $R_2$ are independently chosen from a hydrogen atom and mono- or polyhydroxyalkyl radicals. For example, the meta-aminophenols of the compounds of formula (III) may be chosen from 5-amino-2-methylphenol and 5-[N-(β-hydroxyethyl)amino]-2-methylphenol.

In at least one embodiment of the present disclosure, the at least one first coupler chosen from meta-aminophenols is chosen from chlorinated meta-aminophenols. As used herein, the term, "chlorinated meta-aminophenol," means a meta-aminophenol comprising in its structure at least one chlorine atom. As a non-limiting example of a chlorinated meta-aminophenol, mention is made of 6-chloro-2-methyl-5-aminophenol.

In at least one embodiment, the at least one first coupler chosen from meta-aminophenols is present in an amount, for each if there are more than one, ranging from 0.001% to 10%, for example from 0.005% to 6% by weight, relative to the total weight of the composition.

The composition of the present disclosure may further comprise at least one additional oxidation base chosen from bis(phenyl)alkylenediamines, para-aminophenols, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, and the addition salts thereof.

As examples of bis(phenyl)alkylenediamines, non-limiting mention may be made of N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

As examples of suitable para-aminophenols, non-limiting mention is made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

As examples of suitable ortho-aminophenols, non-limiting mention may be made of 2-aminophenol, 2-amino-5-methylphenol, 2-amino-6-methylphenol, 5-acetamido-2-aminophenol, and the addition salts thereof.

As examples of suitable heterocyclic bases, non-limiting mention may be made of pyridine derivatives, pyrimidine derivatives and pyrazole derivatives.

As examples of suitable pyridine derivatives, non-limiting mention may be made of the compounds described in British Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof.

As examples of other suitable pyridine oxidation bases that are useful in the present disclosure, non-limiting mention may be made of the 3-aminopyrazolo-[1,5-a]pyridine oxidation bases or the addition salts thereof described, for example, in French Patent Application No. FR 2 801 308. For example, non-limiting mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and the addition salts thereof.

As examples of suitable pyrimidine derivatives, non-limiting mention may be made of the compounds described, for example, in German Patent No. DE 23 59 399; Japanese Patent Application Nos. JP 88-169 571 and JP 05 163 124; European Patent Application No. EP 0 770 375; and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048, for example pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, the addition salts thereof, and the tautomeric forms thereof, when a tautomeric equilibrium exists.

As examples of suitable pyrazole derivatives, non-limiting mention may be made of the compounds described in German Patent Nos. DE 38 43 892 and DE 41 33 957; International Patent Application Nos. WO 94/08969 and WO 94/08970; French Patent Application No. FR-A-2 733 749; and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

In at least one embodiment of the present disclosure, when the composition comprises at least one additional oxidation base, they are each present in the composition in an amount ranging from 0.001% to 10%, for example from 0.005% to 6% by weight, relative to the total weight of the composition.

In at least one embodiment, the composition of the present disclosure may comprise at least one additional coupler chosen from meta-phenylenediamines, meta-diphenols, naphthalene-based couplers and heterocyclic couplers, and the addition salts thereof.

As examples of such additional couplers, non-limiting mention may be made of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

In at least one embodiment of the present disclosure, when the composition comprises at least one additional coupler, they are each present in an amount ranging from 0.001% to 10%, for example from 0.005% to 6% by weight, relative to the total weight of the composition.

In at least one embodiment of the present disclosure, the addition salts of the oxidation bases and of the couplers that may be used herein are chosen from acid addition salts, such as hydrochlorides, hydrobromides, sulfates, citrates, succinates, tartrates, lactates, ($C_1$-$C_4$)alkylsulfonates, tosylates, benzenesulfonates, phosphates and acetates, and basic addition salts, such as sodium hydroxide, potassium hydroxide, ammonia, amines or alkanolamines.

The at least one oxidizing agent may be chosen, for example, from oxidizing agents conventionally used for the oxidation dyeing of keratin fibers. As examples of such oxidizing agents, non-limiting mention may be made of hydrogen peroxide, urea peroxide, alkali metal bromates, persalts such as perborates and persulfates, peracids and oxidase enzymes, among which non-limiting mention may be made of peroxidases, 2-electron oxidoreductases such as uricases and 4-electron oxygenases, for instance laccases, the oxidase enzymes optionally being in the presence of the cofactors thereof. In at least one embodiment, hydrogen peroxide is used as the at least one oxidizing agent.

In at least one embodiment, the at least one oxidizing agent is present in an amount ranging from 0.01% to 30%, for example from 0.1% to 20% by weight, relative to the total weight of the composition.

In at least one embodiment, the pH of the dye composition described herein ranges from 5.5 to 7.5, for example from 5.7 to 6.9. The pH may be adjusted to a desired value by means of acidifying or basifying agents typically used in the dyeing of keratin fibers, or alternatively by using standard buffer systems.

As examples of suitable acidifying agents, non-limiting mention may be made of inorganic and organic acids, such as hydrochloric acid, orthophosphoric acid, sulfuric acid, carboxylic acids such as acetic acid, tartaric acid, citric acid and lactic acid, and sulfonic acids.

As examples of suitable basifying agents, non-limiting mention may be made of aqueous ammonia, alkaline carbonates, alkanolamines such as mono-, di- and triethanolamine and derivatives thereof, sodium hydroxide, potassium hydroxide and the compounds of formula (V) below:

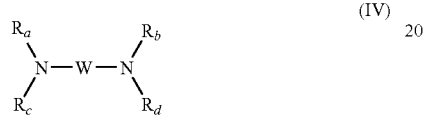

(IV)

in which W is a propylene residue that is optionally substituted with a hydroxyl group or a $C_1$-$C_4$ alkyl radical; $R_a$, $R_b$, $R_c$ and $R_d$, which may be identical or different, are independently chosen from a hydrogen atom, $C_1$-$C_4$ alkyl radicals, and $C_1$-$C_4$ hydroxyalkyl radicals.

The medium that is suitable for dyeing, also known as the dye support, is a cosmetic medium that generally comprises water or a mixture of water and at least one organic solvent to dissolve the compounds that are not sufficiently soluble in water. As examples of suitable organic solvents, non-limiting mention may be made of $C_1$-$C_4$ lower alkanols such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

In at least one embodiment, the at least one organic solvent is present in an amount ranging from 1% to 40%, for example from 5 to 30% by weight, relative to the total weight of the dye composition.

The dye composition in accordance with the present disclosure may further comprise various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, such as anionic, cationic, nonionic or amphoteric associative polymeric thickeners, antioxidants, penetrants, sequestrants, fragrances, buffers, dispersants, conditioning agents, such as silicones, which may be volatile or nonvolatile, and modified or unmodified, film-forming agents, ceramides, preserving agents, and opacifiers.

In at least one embodiment, the adjuvants, if used, are each present in an amount ranging from 0.01% to 20% by weight, relative to the weight of the composition.

Of course, a person skilled in the art will take care to select this or these optional additional compounds such that the advantageous properties intrinsically associated with the oxidation dye composition in accordance with the present disclosure are not, or are not substantially, adversely affected by the addition(s) envisaged.

The dye composition according to the present disclosure may be in various forms, such as in the form of a liquid, a creams, a gel, or in any other form suitable for dyeing keratin fibers such as human hair.

In at least one embodiment, the process in accordance with the present disclosure comprises applying the composition described herein to keratin fibers for a time that is sufficient to develop a desired coloration, after which the fibers are rinsed, optionally washed with shampoo, rinsed again and dried.

In at least one embodiment, the time required to develop a desired coloration on the keratin fibers ranges from 2 to 60 minutes, for example from 3 to 40 minutes, such as from 5 to 30 minutes.

In at least one embodiment, the process of the present disclosure comprises a first step that comprises separately storing:

a composition (A) comprising, in a medium suitable for dyeing, at least one first oxidation base chosen from 2,3-diamino-6,7-dihydro-1H,5H-pyrazolo[1,2-a]pyrazol-1-one and addition salts thereof, at least one second oxidation base chosen from para-phenylenediamines and at least one first coupler chosen from meta-aminophenols; and a composition (B) containing, in a suitable dyeing medium, at least one oxidizing agent; and mixing composition (A) and composition (B) together at the time of use before applying this mixture to the keratin fibers.

Compositions (A) and (B) may also contain various adjuvants conventionally used in hair dye compositions and as defined above.

The pH of composition (A) may range from 3 to 12, for example from 5 to 11. The pH may be adjusted to the desired value by means of acidifying or basifying agents, or alternatively by using standard buffer systems, as described herein.

The pH of composition (B) is such that, after mixing with composition (A), the pH of the resulting composition applied to the keratin fibers ranges from 5.5 to 7.5, for example from 5.6 to 6.9. The pH of composition (B) may be adjusted to a desired value by means of acidifying or basifying agents, or alternatively by using standard buffer systems, as described herein.

The present disclosure also provides a multi-compartment dyeing device or "kit" or any other multi-compartment conditioning system, comprising a first compartment containing composition (A) as described herein and a second compartment containing composition (B) as described herein. These devices may be equipped with a means for applying the desired mixture to the hair, such as the devices described in French Patent No. FR-2 586 913.

The present disclosure also provides uses of a composition according to the present disclosure for the oxidation dyeing of keratin fibers, including human keratin fibers such as the hair.

Other than in the operating examples, or where otherwise indicated, all numbers expressing quantities of ingredients, reaction conditions, and so forth in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches. Also, where a range is given, even if the term "between" is used, the ranges defined include the stated endpoints.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The example that follows serve to illustrate the invention without, however, being limiting in nature.

EXAMPLE

The following composition was prepared:

| | |
|---|---|
| Sequestrants | 2 g |
| Reducing agents | 0.71 g |
| Ethanolamine | 1.6 g |
| Citric acid | 0.15 g |
| Fumed silica of hydrophobic nature | 1.2 g |
| 2,3-Diamino-6,7-dihydro-1H,5H-pyrazolo[1,2-a]pyrazol-1-one•2 CH$_3$-SO$_3$H | 1.5 g |
| 4-Amino-2-hydroxytoluene | 1.1 g |
| 6-Hydroxyindole | 0.2 g |
| para-Phenylenediamine | 0.4 g |
| Glycol distearate | 2 g |
| Fragrance | 0.95 g |
| Tetramethylhexamethylenediamine/ 1,3-dichloropropylene polycondensate | 4 g |
| Dimethyldiallylammonium chloride/ acrylic acid copolymer (80/20) | 3 g |
| Carbopol 980 | 0.4 g |
| Water | 35.04 g |
| Propylene glycol | 10 g |
| Lauric acid | 3 g |
| Oxyethylenated lauryl alcohol (12 EO) | 7 g |
| Cetylstearyl alcohol | 11.5 g |
| Oxyethylenated decyl alcohol (3 EO) | 10 g |
| Oxyethylenated oleocetyl alcohol (30 EO) | 4 g |
| Ascorbic acid | 0.25 g |

At the time of use, 1-part by weight of the composition described above was mixed with 1 part by weight of a 20-volumes hydrogen peroxide solution whose pH was equal to 2.3. A final pH of 6.8±0.2 was obtained.

The mixture obtained was applied to locks of natural or permanent-waved grey hair containing 90% white hairs. After a leave-on time of 20 minutes at 22° C.±3° C., the locks were rinsed, washed with a standard shampoo, rinsed again and then dried.

The hair coloration was evaluated visually. A shade with a strong mahogany tint was obtained.

What is claimed is:

1. A composition for dyeing keratin fibers, comprising, in a suitable dyeing medium:
    at least one first oxidation base chosen from 2,3-diamino-6,7-dihydro-1H,5H-pyrazolo[1,2-a]pyrazol-1-one of formula (I) below, and the addition salts thereof:

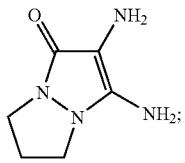

(I)

at least one second oxidation base chosen from para-phenylenediamines chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-pheneylenediamine, and the addition salts thereof with an acid;
    at least one first coupler chosen from meta-aminophenols;
    at least one additional coupler chosen from meta-phenylenediamines, meta-diphenols, naphthalene-based couplers and heterocyclic couplers, and the addition salts thereof; and
    at least one oxidizing agent;
    wherein the pH of the composition ranges from 5.5 to 7.5; and further wherein the at least one first coupler and the at least one additional coupler are each present in an amount ranging from 0.001% to 10% by weight, relative to the total weight of the composition.

2. The composition of claim 1, wherein said at least one first oxidation base is present in an amount ranging from 0.001% to 10% by weight, relative to the total weight of the composition.

3. The composition of claim 1, wherein the at least one second oxidation base is present in an amount, for each if more than one is present, ranging from 0.001% to 10% by weight relative to the total weight of the dye composition.

4. The composition of claim 1, wherein said at least one first coupler is chosen from compounds of formula (III) below, and the addition salts thereof:

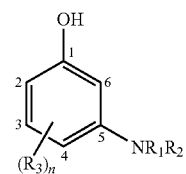

(III)

wherein:
    $R_1$ and $R_2$, which may be identical or different, are chosen from a hydrogen atom; alkyl radicals; monohydroxyalkyl radicals; polyhydroxyalkyl radicals; and monoaminoalkyl radicals; or
    $R_1$ and $R_2$ form, together with the nitrogen atom to which they are attached, a saturated or unsaturated, 5- to 7-membered cyclic group containing at least one heteroatom, which may be unsubstituted or substituted with at least one radical chosen from carboxyl, carboxamido, hydroxyl, amino, monoalkylamino, and dialkylamino radicals, and alkyl radicals optionally substituted with at least one radical chosen from hydroxyl, amino, monoalkylamino and dialkylamino radicals;

n is an integer ranging from 0 to 3; and each $R_3$, if present, is independently chosen from a halogen atom; an alkyl radical; an alkoxy radical; a monohydroxyalkyl radical; a polyhydroxyalkyl radical; a monohydroxyalkoxy radical; and a polyhydroxyalkoxy radical.

5. The composition of claim 4, wherein $R_1$ and $R_2$, independently of each other, are chosen from a hydrogen atom, monohydroxyalkyl radicals, and polyhydroxyalkyl radicals.

6. The composition of claim 1, wherein said at least one first coupler is chosen from chlorinated meta-aminophenols.

7. The composition of claim 1, further comprising at least one additional oxidation base chosen from bis(phenyl)alkylenediamines, para-aminophenols, bis-para-aminophenols, ortho-aminophenols, ortho-phenylenediamines and heterocyclic bases other than 2,3-diamino-6,7-dihydro-1H,5H-pyrazolo[1,2-a]pyrazol-1-one, and the addition salts thereof.

8. The composition of claim 1, wherein said at least one oxidizing agent is chosen from hydrogen peroxide, urea peroxide, alkali metal bromates, persalts, peracids and oxidase enzymes.

9. The composition of claim 1, wherein said at least one oxidizing agent is present in an amount ranging from 0.01% to 30% by weight, relative to the total weight of the composition.

10. A process for dyeing keratin fibers, comprising applying to said keratin fibers a dyeing composition for a time that is sufficient to develop a desired coloration;

rinsing the fibers;

optionally washing the fibers with shampoo;

optionally rinsing the fibers again; and drying the fibers, wherein said dyeing composition comprises, in a suitable dyeing medium:

at least one first oxidation base chosen from 2,3-diamino-6,7-dihydro-1H,5H-pyrazolo[1,2-a]pyrazol-1-one of formula (I) below, and the addition salts thereof:

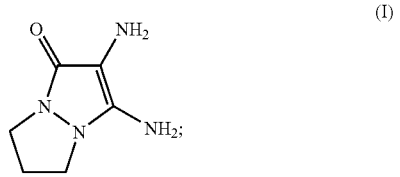

at least one second oxidation base chosen from para-phenylenediamines chosen from para-phenylenediamine, para-tolylenediamine, 2-isopropyl-para-phenylenediamine, 2-β-hydroxyethyl-para-phenylenediamine, 2-βhydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-pheneylenediamine, and the addition salts thereof with an acid;

at least one first coupler chosen from meta-aminophenols;

at least one additional coupler chosen from meta-phenylenediamines, meta-diphenols, naphthalene-based couplers and heterocyclic couplers, and the addition salts thereof; and at least one oxidizing agent;

wherein the pH of said dyeing composition ranges from 5.5 to 7.5; and further wherein the at least one first coupler and the at least one additional coupler are each present in an amount ranging from 0.001% to 10% by weight, relative to the total weight of said dyeing composition.

11. A process for dyeing keratin fibers, comprising separately storing a composition (A) comprising, in a suitable dyeing medium, at least one first oxidation base chosen from 2,3-diamino-6,7 dihydro-1H,5H-pyrazolo[1,2-a]pyrazol-1-one of formula (I) below, and the addition salts thereof:

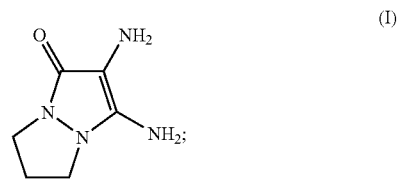

at least one second oxidation base chosen from para-phenylenediamines chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-pheneylenediamine, and the addition salts thereof with an acid;

at least one first coupler chosen from meta-aminophenols; and at least one additional coupler chosen from meta-phenylenediamines, meta-diphenols, naphthalene-based couplers and heterocyclic couplers, and the addition salts thereof; and a composition (B) comprising, in a medium suitable for dyeing, at least one oxidizing agent;

mixing said composition (A) and composition (B) together at or before the time of use, wherein the pH of said mixture ranges from 5.5 to 7.5 and further wherein the at least one first coupler and the at least one additional coupler are each present in an amount ranging from 0.001% to 10% by weight, relative to the total weight of said mixture; and applying said mixture to said keratin fibers for a time that is sufficient to develop a desired coloration;

rinsing the fibers;

optionally washing the fibers with shampoo;

optionally rinsing the fibers again; and drying the fibers.

12. A multi-compartment device, comprising:

a first compartment comprising a composition (A) comprising, in a suitable dyeing medium, at least one first oxidation base chosen from 2,3-diamino-6,7-dihydro-1H,5H-pyrazolo[1,2-a]pyrazol-1-one of formula (I) below, and the addition salts thereof:

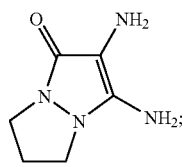 (I)

at least one second oxidation base chosen from para-phenylenediamines chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-pheneylenediamine, and the addition salts thereof with an acid;

at least one first coupler chosen from meta-aminophenols; and at least one additional coupler chosen from meta-phenylenediamines, meta-diphenols, naphthalene-based couplers and heterocyclic couplers, and the addition salts thereof; and a second compartment comprising a composition (B) comprising, in a medium suitable for dyeing, at least one oxidizing agent.

* * * * *